United States Patent [19]

Horikoshi et al.

[11] 4,052,262
[45] Oct. 4, 1977

[54] PREPARATION OF AN ALKALINE PROTEASE

[75] Inventors: Koki Horikoshi, Saitama; Yonosuke Ikeda, Tokyo, both of Japan

[73] Assignee: Rikagaku Kenkyusho, Japan

[21] Appl. No.: 40,771

[22] Filed: May 27, 1970

[30] Foreign Application Priority Data

| | | |
|---|---|---|
| May 31, 1969 | Japan | 44-42646 |
| Dec. 15, 1969 | Japan | 44-100818 |
| Apr. 22, 1970 | Japan | 45-34535 |

[51] Int. Cl.² .................. C12D 13/10; C07G 7/02
[52] U.S. Cl. ................ 195/66 R; 195/62; 252/DIG. 12
[58] Field of Search ............ 195/62–69, 195/100; 252/DIG. 12

[56] References Cited

U.S. PATENT DOCUMENTS

| | | | |
|---|---|---|---|
| 3,352,761 | 11/1967 | Moses | 195/100 X |
| 3,576,719 | 4/1971 | Murao | 195/62 |
| 3,723,250 | 3/1973 | Aunstrap et al. | 195/62 |

FOREIGN PATENT DOCUMENTS

1,800,508  5/1969  Germany

OTHER PUBLICATIONS

Tsuru, et al., Studies on Bacterial Protease, Agr. Biol. Chem., vol. 30, No. 12, 1966 (pp. 1261–1268) 5583A37.
Keay, et al., Differentiation of Alkaline Proteases from Bacillus Species, Biochemical and Biophysical Research Communications, vol. 34, No. 5, 3/1969 (pp. 600–604)

*Primary Examiner*—David M. Naff
*Attorney, Agent, or Firm*—Bucknam and Archer

[57] ABSTRACT

An alkaline protease is produced by cultivation of novel microorganism strains belonging to the Bacillus genus. The alkaline protease has optimum pH of 11 to 12 and is useful as an additive for detergents.

4 Claims, 8 Drawing Figures

PREPARATION OF AN ALKALINE PROTEASE

BACKGROUND OF THE INVENTION

This invention relates to a high unit, novel alkaline protease and a very advantageous manufacture of the same by cultivation of a novel microorganism producing alkaline protease in an alkaline culture medium containing a carbonate or a culture medium not containing sugars.

Various methods for the manufacture of protease, a protein-decomposing enzyme, having optimal pH in the alkaline side, are known, but methods for the production of a large quantity of alkaline protease using a microorganism and the special media and culture conditions as in the present invention have not been described in the literature.

The present invention is characterized in the microorganism used and its culture conditions for production of a large quantity of novel alkaline protease.

The microorganisms used in the present invention show good growth under culture conditions to be described in detail below, and produce the alkaline protease of the present invention. They are new strains belonging to the Bacillus genus, Bacillus sp. No. 221, Bacillus sp. No. 0–4 and Bacillus sp. No. Y-76. The said Bacillus sp. No. 221, Bacillus sp. No. 0–4 and Bacillus sp. No. Y-76 have been discovered by the present inventors.

Each of the said strains, Bacillus sp. No. 221, Bacillus sp. No. 0–4 and Bacillus sp. No. Y-76 which are employed in the process of the invention, is isolated from the soil collected in the Yamato-machi district of Kitaadachi-gun, Saitama Prefecture, Japan.

The isolation of the microorganisms, Bacillus sp. No. 221, Bacillus sp. No. 0–4 and Bacillus sp. No. Y-76 was carried out by a procedure described hereinbelow.

The soil from the district mentioned above was suspended in sterilized water and plated on the following medium:

| (Medium composition) | | |
|---|---|---|
| a) | Soluble starch | 20 g |
| | $K_2HPO_4$ | 1 g |
| | Yeast extract | 5 g |
| | Peptone | 5 g |
| | $MgSO_4.7H_2O$ | 0.2 g |
| | Agar | 20 g |
| | Water | 900 ml |
| b) | $Na_2CO_3$ | 10 g |
| | Water | 100 ml |
| (After sterilization at 115° C for 15 min., a) and b) were mixed.) | | |

The plate was incubated at 37° C for 24 to 48 hours.

Thus, a colony of a microorganism which produced a large amount of the said alkaline protease was isolated from colonies on the plate.

This microorganism was called "Bacillus sp. No. 221." The said Bacillus sp. No. 0–4 and Bacillus sp. No. Y-76 were also isolated by the same method.

The strains identified as said Bacillus sp. No. 221, Bacillus sp. No. 0–4 and Bacillus sp. No. Y-76 have been deposited with the American Type Culture Collection (ATCC) 12301 Parklawn Drive, Rockville, Maryland, as ATCC access numbers 21522, 21536 and 21537, respectively, and are on deposit with ATCC as unrestricted deposits permitting the public full access to the cultures. The strains are released for distribution to the public as of Apr. 22, 1970, May 5, 1970 and May 5, 1970, respectively. The present inventors found that the said microorganisms, Bacillus sp. No. 221, Bacillus sp. No. 0–4 and Bacillus sp. No. Y-76 produce and accumulate a high unit of novel alkaline protease under the culture conditions which will be described hereinbelow, and succeeded in establishing the process for the manufacture of the alkaline protease of the present invention. This alkaline protease is very useful as an additive for detergents.

The said Bacillus sp. No. 221, Bacillus sp. No. 0–4 and Bacillus sp. No. Y-76 have the following properties: The microbiological properties were tested by the methods described in "Aerobic Spore-forming Bacteria" by Nathan R. Smith, R. E. Gordon and F. E. Clark (United States Department of Agriculture, Nov. 1952) and "Bergey's Manual of Determinative Bacteriology" (1957).

| Bacillus sp. No. 221 | | |
|---|---|---|
| (a) Growth in Medium | pH in the medium | |
| Medium | pH 7 | pH 10.2* |
| (1) Bouillon | Growth | Growth |
| (2) Bouillon-agar | " | Good growth |
| (3) Glucose-bouillon | Poor growth | Growth abundant |
| (4) Glucose-bouillon agar | Growth scant | Growth abundant |
| (5) Gelatin medium | — | Good growth |
| (6) Peptone water | Growth | Growth not good |
| (7) Potato medium | Growth | Good growth |

*1% of $Na_2CO_3$ was added

The size of the microorganism is $0.6 - 0.8\mu \times 2.0 - 3.0\mu$; the sporangium is slightly swollen and the spore is oval, $0.8 - 1.0\mu \times 1.3\mu$.

The microorganism has pertrichous flagella, as will be seen in the electron micrograph attached as FIG. 1. The Bacillus grows very well on the medium (glucose, yeast extract, peptone, $K_2HPO_4$, $MgSO_4 7H_2O$ and $Na_2CO_3$, pH 10.2) to be described below, as a white colony. The characteristic of this Bacillus is that it grows well in an alkaline medium rather than in a neutral medium in which no sugar is contained. b. Physiological Properties 1. Optimal Growth Conditions: pH 8–10 Temperature: 37° – 40° C Aerobic
2. Conditions under which the bacteria can grow: pH 7-11 Temperature: up to 55° C Aerobic The following experiments were carried out using the medium containing 1% $Na_2CO_3$.

3. Gram stainability: Positive (changeable)
4. Voges-Proskauer reaction: Negative
5. Nitrate is reduced.
6. Catalase: Positive
7. Hydrolysis of gelatine and casein: Positive
8. Hydrolysis of starch: Weak
9. Utilization of citrate: Utilized
10. Utilization of ammonium salts: Utilized
11. Growth detected in 5% sodium chloride solution.
12. Growth detected on glucose-nitrate medium.
13. No growth under anaerobic conditions.
14. No production of gas in nitrate medium under anaerobic conditions.
15. Growth detected in a glucose-asparagine medium.

c. Utilization of Carbon Source

The microorganism utilizes glucose, mannose, salicin, cellobiose, lactose, sucrose, arabinose, mannitol, and xylose in a medium containing 1% carbonate but production of acid is not clear due to the presence of a large quantity of carbonate.

| *Bacillus* sp. No. 0-4 | | |
|---|---|---|
| (a) Growth in Medium | pH in the medium | |
| Medium | pH 7 | pH 10.2* |
| (1) Bouillon | Poor growth | Growth |
| (2) Bouillon-agar | " | Good growth |
| (3) Glucose-bouillon | " | " |
| (4) Glucose-bouillon agar | Growth | " |
| (5) Gelatin medium | — | " |
| (6) Peptone water | — | Growth not good |
| (7) Potato medium | Growth | Good growth |

*1% of $Na_2CO_3$ was added

The size of the microorganism is $0.5 - 0.7\mu \times 2.0 - 3.0\mu$; the sporangium is slightly swollen and the spore is oval, $0.7 - 1.0\mu \times 1.2 - 1.3\mu$.

The microorganism has pertrichous flagella, as will be seen in the electron micrograph attached as FIG. 2. The said Bacillus grows very well in the medium (soluble starch, yeast extract, peptone, $K_2HPO_4$, $MgSO_4 7H_2O$ and $Na_2CO_3$, adjusted at pH 10.2) to be described below as a white colony. The characteristic of this Bacillus is that it grows well in an alkaline medium rather than in a neutral medium.

b. Physiological Properties
1. Optimal Growth Conditions: pH 8–10 Temperature: 37° – 40° C Aerobic
2. Conditions under which the bacteria can grow: pH 6.0 – 11 Temperature: up to 56° C Aerobic The following experiments were carried out using the medium containing 1% $Na_2CO_3$.
3. Gram stainability: Positive (changeable)
4. Voges-Proskauer reaction: ±
5. Nitrate is reduced.
6. Catalase: Positive
7. Hydrolysis of gelatine and casein: Positive
8. Hydrolysis of starch: Weak
9. Utilization of citrate: Utilized
10. Utilization of ammonium salts: Utilized
11. Poor growth detected in 7% sodium chloride solution.
12. Growth scanty in a glucose-nitrate medium.
13. No growth under anaerobic conditions.
14. No production of gas in nitrate medium under anaerobic conditions.
15. Growth detected in a glucose-asparagine medium.

c. Utilization of Carbon Source

The microorganism utilizes glucose, mannose, salicin, cellobiose, lactose, sucrose, arabinose, mannitol, and xylose in a medium containing 1% carbonate but production of acid is not clear due to the presence of a large quantity of carbonate.

| *Bacillus* sp. No. Y-76 | | |
|---|---|---|
| (a) Growth in Medium | pH in the medium | |
| Medium | pH 7 | pH 10.2* |
| (1) Bouillon | Growth | Growth |
| (2) Bouillon-agar | " | " |
| (3) Glucose-bouillon | " | Uniform turbidity, good growth |
| (4) Glucose-bouillon agar | " | Good growth |
| (5) Gelatin medium | — | Good growth liquified |
| (6) Peptone water | — | Growth not good |
| (7) Potato medium | Growth | Good growth |

*1% of $Na_2CO_3$ was added

The size of the microorganism is $0.5 - 0.7\mu \times 2.0 - 3.0\mu$; the sporangium is slightly swollen and the spore is oval, $0.7 - 1.0\mu \times 1.2 - 1.3\mu$.

The microorganism has pertrichous flagella, as will be seen in the electron micrograph attached as FIG. 3. The said Bacillus grows very well in the medium (soluble starch, yeast extract, peptone, $K_2HPO_4$, $MgSO_4 7H_2O$ and $Na_2CO_3$, adjusted at pH 10.2) to be described below, as a white colony. The characteristic of this Bacillus is that it grows well in an alkaline medium rather than neutral medium.

b. Physiological Properties
1. Optimal Growth Conditions: pH 8 – 10 Temperature: 37° – 40° C Aerobic
2. Conditions under which the bacteria can grow: pH 6.0-11 Temperature: up to 56° C Aerobic The following experiments were carried out using the medium containing 1% $Na_2CO_3$.
3. Gram stainability: Positive (changeable)
4. Voges-Proskauer reaction: ±
5. Nitrate is reduced.
6. Catalase: Positive
7. Hydrolysis of gelatine and casein: Positive
8. Hydrolysis of startch: Positive
9. Utilization of citrate: Utilized
10. Utilization of ammonium salts: Utilized
11. Growth detected in 7% sodium chloride solution.
12. Growth detected on glucose-nitrate medium.
13. No growth under anaerobic conditions.
14. No production of gas in nitrate medium under anaerobic conditions.
15. Growth detected on glucose-asparagine medium.

c. Utilization of Carbon Source

The microorganism utilizes glucose, mannose, salicin, cellobiose, lactose, sucrose, arabinose, mannitol, and xylose in a medium containing 1% carbonate but production of acid is not clear due to the presence of a large quantity of carbonate.

Next, the said microorganisms, Bacillus sp. No. 221, Bacillus sp. No. 0-4 and Bacillus sp. No. Y-76 are different from each other, and their characteristic different points are shown in the following table:

| Microorganisms Properties | *Bacillus* sp. No. 221 | *Bacillus* sp. No. 0-4 | *Bacillus* sp. No. Y-76 |
|---|---|---|---|
| Growth in neutral medium | Very poor growth | Poor growth | Growth |
| Growth in NaCl 7% | Slow growth | Poor growth | Good growth |
| Growth in glucose-asparagine medium | Very slow growth | Growth | Growth |
| Voges-Proskauer reaction | Negative | ± | ± |
| Growth at 56° C | Growth | Very poor growth | Poor growth |
| Membranes formation | No formation | No formation | Formation |

As shown in the above table, it is clear that the said microorganisms are not identical to each other in their characteristics.

Then, comparative examinations of the said Bacillus sp. No. 221, Bacillus sp. No. 0-4 and Bacillus sp. No. Y-76 according to the method of classification described in the said "Aerobic Spore-forming Bacteria" and "Bergey's Manual of Determinative Bacteriology" (1957) (from p. 612, et seq.) showed that the said microorganisms had some property similar to the known microorganisms belonging to the Bacillus sp., but were entirely different in characteristic properties, and there were no species among the known genus which agreed with the afore-mentioned properties. It was, therefore, concluded that they would be appropriate to establish new strains of the Bacillus sp. Since the said microorganisms are each an aerobic, spore-forming bacteria, it is clear that it should belong to the Bacillus genus. The highly characteristic property of the said microorganisms is that the growth is especially good in an alkaline medium, the optimal pH being 8 – 10.

Some examinations were made on known bacterial species in relation to Bacillus sp. No. 221, and *Bacillus subtilis* may be cited as a comparative organism. *Bacillus subtilis* is positive to the Vogel-Proskauer reaction, and has an optimal pH of 5 – 8 in a medium containing glucose. In contrast, Bacillus sp. No. 221 is negative to the Vogel-Proskauer reaction, and shows poor growth in a medium containing glucose at pH 7, the optimal being around pH 10. In these respects, Bacillus sp. No. 221 is clearly discriminated from *Bacillus subtilis.*

*Bacillus brevis* may also be cited as a comparative organism for each of Bacillus sp. No. 221, Bacillus sp. No. 0-4 and Bacillus sp. No. Y-76. However, *Bacillus brevis* has no ability to hydrolyze starch, produces gas in a nitrate medium under anaerobic conditions, and its gram stainability is varied, usually being negative. In contrast, Bacillus sp. No. 221, Bacillus sp. No. 0-4 and Bacillus sp. No. Y-76 have each a slight ability to hydrolyze starch, do not produce gas in a nitrate medium under anaerobic conditions, and are invariably positive in gram staining. The most characteristic difference in their properties is that whereas *Bacillus brevis* has pH 8.0 – 8.6 as its growth condition but does not grow at all at pH 10, Bacillus sp. No. 221, Bacillus sp. No. 0-4 and Bacillus sp. No. Y-76 grow at pH 7 – 11. Growth of each of Bacillus sp. No. 221, Bacillus sp. No. 0-4 and Bacillus sp. No. Y-76 is very slow at pH 7 in the presence of glucose, and the pH of around 10 is optimal. In this respect, each of Bacillus sp. No. 221, Bacillus sp. No. 0-4 and Bacillus sp. No. Y-76 is clearly distinguished from *Bacillus brevis.*

Since growth of Bacillus sp. No. 221 was inhibited by glucose, it may be compared with *Bacillus firmus.* The growth of these two microorganisms on citrate medium and the optimal temperature of their growth are different. In addition, Bacillus sp. No. 221 shows glucose inhibition at pH 7, but at pH 10 no growth inhibition by glucose is detected, however, *Bacillus firmus* does not grow at pH 10, irrespective of the presence or absence of glucose. In these respect, the two microorganisms are clearly distinguished.

Consequently, it is appropriate to establish a new species for each of the said microorganisms, Bacillus sp. No. 221, Bacillus sp. No. 0-4 and Bacillus sp. No. Y-76.

According to the process of the present invention, the alkaline protease of the present invention can be produced using not only Bacillus sp. No. 221, Bacillus sp. No. 0-4 and Bacillus sp. No. Y-76, described above, but also natural and artificial mutants thereof producing the said alkaline protease.

In the practice of the present invention, the fermentation may be carried out according to the following method.

First, there are two methods for the preparation of the culture medium used in the present invention.

The first method is characterized by the addition of carbonate to the composition of the culture medium. In this medium, glucose, starch, dextrin, maltose, fructose, and the like are used as the carbon source. Yeast extract, peptone, corn-steep liquor, and the like are used as the nitrogen source. Various carbonates, such as potassium carbonate, sodium carbonate, and sodium bicarbonate are used as the inorganic salts and added to the solution to prepare the culture medium which is adjusted to about pH 10.5.

The second method is characterized by the elimination of glucose and starch from the composition of the culture medium. In this case, a carbonate may be added to the culture medium as an inorganic salt. Yeast extract, peptone, corn-steep liquor, and the like are used as the nitrogen source, and various carbonates such as potassium carbonate, sodium carbonate, and sodium bicarbonate are used as the inorganic salts and may be added to the solution of the former to prepare the culture medium which is adjusted to about pH 7.

The medium thus prepared is inoculated with the strain of a microorganism selected from the group consisting of Bacillus sp. No. 221, Bacillus sp. No. 0-4 and Bacillus sp. No. Y-76, and cultured with shaking at a temperature of about 24° – 45° C. In general, the activity of the enzyme produced reaches a maximum after about 24 – 75 hours, e.g., 30 – 50 hours, of culture.

Since the period required to reach the maximum enzyme activity may vary according to the aeration and stirring conditions, even when the same temperature and culture medium of the same components are used, it is advisable to decide the period of culture by measuring the enzyme activity in each case.

The second important condition is the pH value of the medium. It is necessary to adjust the initial pH value within the range of 6 to 11 with carbonate or bicarbonate salts. Further, the optimal pH value when using a culture medium containing sugars is 8 to 11, while the pH of 6 to 10 is the optimal when glucose has been eliminated from the culture medium.

The commonly used physicochemical methods can be employed for the isolation of the enzyme from the culture broth. For example, after cooling the culture broth, acetic acid is added or not added to the culture broth to neutralize it, and ethanol is then added to precipitate the enzyme, alkaline protease, quantitatively. The precipitate is then collected, thoroughly washed with ethanol, and dried. The enzyme, alkaline protease, thus obtained from the culture of the said microorganisms is confirmed to be an alkaline protease having the optimum pH of about 11.5 and retaining the activity, even when heated at 50° C for 1 hour.

As the culture condition, it is necessary to have an alkaline medium containing a high concentration of carbonate. Various carbonates are added to the medium containing a composition such as the carbon source and nitrogen source necessary fot the growth of the microorganism. For example, it is necessary to make a medium containing glucose, $K_2HPO_4$, yeast extract, peptone, and $MgSO_4.7H_2O$, with the addition of sodium carbonatee, potassium carbonate, or sodium bicarbonate. It is desirable to make the concentration of the carbonate added to 0.5 – 5%.

For the advantageous production of the objective alkaline protease, addition of a carbonate to the above medium is an extremely important condition and the following fact is proved from experimental results.

The growth of the microorganism used, Bacillus sp. No. 221, and production of protease were examined by the use of the foregoing medium with 1% of sodium carbonate or 1% each of various carbonates, and the same medium from which the carbonate was eliminated and in its place 1% of sodium chloride or potassium chloride, and adjusted to pH 10.0 with sodium hydroxide. Growth of the microorganism (said Bacillus sp. No. 221) was tested by taking the culture broth after 18 hours into a cuvette of 1 cm light path and measuring its absorbance at 660 mμ, and protease activity was measured under the conditions described hereinbelow. These results are listed in Table 1, which indicates that the presence of a carbonate in the medium is an important factor for the production of the alkaline protease of the present invention.

Table 1

| Glucose concentration | Salt added | Initial pH | Final pH | Growth | Protease activity (U/ml) |
|---|---|---|---|---|---|
| 1 | None (Only containing glucose, $K_2HPO_4$, yeast extract, peptone, and $MgSO_4 \cdot 7H_2O$) | 7.2 | 6.5 | 0.1 | <100 |
| 1 | KCl 1% | 10.5 (adjusted with NaOH) | — | 0.5 | <100 |
| 1 | NaCl 1% | 10.5 (adjusted with NaOH) | — | 0.45 | <100 |
| 1 | $Na_2HPO_4$—NaOH 0.05M | 10.5 | — | 0.8 | 750 |
| 1 | $NaHCO_3$ 1.0% | 10.0 | 8.5 | 1.2 | 1400 |
| 1 | $Na_2CO_3$ 0.5% | 10.2 | 8.8 | 1.2 | 1800 |
| 1 | $Na_2CO_3$ 1.0% | 10.5 | 9.3 | 1.2 | 2800 |
| 1 | $K_2CO_3$ 1.0% | 10.5 | 9.2 | 1.15 | 1500 |

Next, the growth of the microorganism used, Bacillus sp. No. 0–4, and production of protease were examined by the use of the foregoing medium with 1% of sodium carbonate or 1% each of various carbonates, and the same medium from which the carbonate was eliminated and in its place 1% of sodium chloride or potassium chloride, and adjusted to pH 10.0 with sodium hydroxide. Growth of the microorganism was tested by taking the culture broth after 18 hours into a cuvette of 1 cm light path and measuring its absorbance at 660 mμ, and protease activity was measured under the condition described in later. These results are listed in Table 2, which indicates that the presence of a carbonate in the medium is an important factor for the production of the alkaline protease of the present invention.

In addition, when the said Bacillus sp. No. Y-76 was used as a test organism, results similar to those of Table 2 were obtained.

Table 2

| Salt added | pH | Growth | Protease activity (U/ml) |
|---|---|---|---|
| None (Only containing soluble starch, $K_2HPO_4$, yeast extract, peptone and $MgSO_4 \cdot 7H_2O$) | 10.0 | 0.8 | 750 |
| KCl | " | 0.9 | " |
| NaCl | " | " | " |
| $Na_2CO_3$ | 10.5 | 1.2 | 71.00 |
| $NaHCO_3$ | 9.0 | " | 51.00 |
| $K_2CO_3$ | 10.5 | 1.1 | 52.00 |

The other medium used in the present invention is a medium not containing any sugar. It is a medium containing components necessary for the growth of microorganism such as carbon source and nitrogen source, such as $K_2HPO_4$, yeast extract, peptone, and $MgSO_4 \cdot 7H_2O$. It is desirable that the pH value be adjusted to 6 – 10.

For the advantageous production of the alkaline protease, the absence of sugars in the foregoing medium is an important condition and this fact is proved by the following experiments.

The growth of the organism used, Bacillus sp. No. 221, and the production of the alkaline protease were examined by the use of the said medium, to which was added sodium carbonate or sodium bicarbonate. The same medium with glucose, with or without sodium carbonate or sodium bicarbonate was tested. The growth of the organism (said Bacillus sp. No. 221) was examined by taking the culture broth after 18 hours in a cuvette of 1 cm light path and measuring its absorbance at 660 mμ, and protease activity was measured under the condition described below. These results are given in Table 3 which indicates that the absence or low concentration of glucose in the medium is an important factor at neutral pH for the production of the alkaline protease of the present invention.

Table 3

| Glucose concentration (%) | Salt (carbonate) concentration(%) | Initial pH | Final pH | Growth | Protease activity (U/ml) |
|---|---|---|---|---|---|
| (When glucose is not added) | | | | | |
| 0 | None (Only $K_2HPO_4$, yeast extract, peptone, $MgSO_4 \cdot 7H_2O$) | 6.8 | 9.3 | 1.1 | 2500 |
|  | $NaHCO_3$ 0.1 | 8.2 | 9.4 | 1.0 | 2700 |
|  | " 0.2 | 8.7 | 9.5 | 0.9 | 2000 |
|  | " 0.3 | 9.1 | 9.6 | 1.0 | 1800 |
|  | $Na_2CO_3$ 0.2 | 9.5 | 9.6 | 0.9 | 1600 |
|  | " 1.0 | 10.6 | 9.8 | 0.8 | 1150 |
| (When glucose is added) | | | | | |
| 0.1 | None (Only glucose, $K_2HPO_4$, yeast extract, peptone, $MgSO_4 \cdot 7H_2O$) | 7.2 | 9.0 | 1.1 | 600 |
|  | $NaHCO_3$ 0.2 | 8.7 | 9.3 | 1.0 | 2600 |
|  | " 0.5 | 9.6 | 9.4 | 1.0 | 2100 |

Table 3-continued

|   |   |   |   |   |   |   |
|---|---|---|---|---|---|---|
|   | " | 1.0 | 10.0 | 9.5 | 0.98 | 2100 |
|   | Na$_2$CO$_3$ | 0.2 | 9.3 | 9.3 | 0.98 | 1800 |
|   | " | 0.4 | 10.0 | 9.5 | 1.1 | 1600 |
|   | "1.0 | 10.5 | 9.5 | 1.05 | 600 |   |
| 0.5 | 0 |   | 7.2 | 6.0 | 0.14 | 100 |
|   | NaHCO$_3$ | 0.2 | 8.6 | 6.4 | 0.40 | 600 |
|   | " | 0.5 | 9.6 | 9.3 | 1.2 | 1600 |
|   | " | 1.0 | 10.0 | 9.3 | 1.15 | 2000 |
|   | Na$_2$CO$_3$ | 0.2 | 9.2 | 9.1 | 1.1 | 1600 |
|   | " | 0.4 | 10.0 | 9.3 | 1.1 | 1100 |
|   | " | 1.0 | 10.5 | 9.6 | 1.15 | 900 |
| 1.0 | Na$_2$CO$_3$ | 1.0% | 7 | (adjusted with HCl or NaOH) | 0.4 | 200 |
|   | " |   | 8 | " | 0.9 | 900 |
|   | " |   | 9 | " | 1.2 | 1500 |
|   | " |   | 10 | " | 1.2 | 2100 |
|   | " |   | 11 | " | 0.7 | 700 |

The next important point in the culture condition is the pH during the culture. From the results of the following experiments, it is necessary to adjust the pH for the production of the alkaline protease to the selected value in the range of 6 to 11. Examination of the effect of pH on the production of alkaline protease by varying the pH of the above culture medium containing 1% of sodium carbonate with HCl or NaOH, as shown in Table 4, indicated that the best result was obtained at pH 7 - 11, especially at pH 8 - 11, in the presence of glucose. In this case, the microorganism used was the said Bacillus sp. No. 221.

Table 4

| pH | Protease Activity (U/ml) | | | | |
|---|---|---|---|---|---|
|   | 7 | 8 | 9 | 10 | 11 |
| Medium Containing 1% Na$_2$CO$_3$ | 220 | 880 | 1,520 | 1,640 | 700 |
| Not containing 1% Na$_2$CO$_3$ | 100 | 100 | 100 | 100 | 100 |

Next, when the said Bacillus sp. No. 0-4 was used, the results as shown in Table 5 were obtained.

Table 5

| pH | Protease Activity (U/ml) | | | | |
|---|---|---|---|---|---|
|   | 6.8 | 8 | 9 | 10 | 11 |
| Medium Containing 1% Na$_2$CO$_3$ | 800 | 3,000 | 5,550 | 6,300 | 2,530 |

From the Table 5, it is noted that the best result is obtained at pH 6 - 11, especially at pH 8 - 11, in the presence of carbonate.

In addition, when the said Bacillus sp. Y-76 was used as a test organism results similar to those of Table 5 were obtained.

The effect of pH on the production of alkaline protease was then examined by varying the pH of the culture medium with NaHCO$_3$ or Na$_2$CO$_3$ and not containing sugars, and the result is shown in Table 6. When glucose was not added, the best result was obtained in a pH range of 6 - 11, especially at 6 - 10. The microorganism used was the said Bacillus sp. No. 221.

Table 6

| Salt added | Initial pH | Final pH | Growth | Protease activity (U/ml) |
|---|---|---|---|---|
| None (only K$_2$HPO$_4$, yeast extract, peptone, MgSO$_4$.7H$_2$O) | 7.0 | 9.3 | 1.2 | 2,100 |
| Na$_2$CO$_3$ 0.5% | 6.8* | 9.2 | 1.1 | 2,000 |
| NaHCO$_3$ 0.1% | 8.2 | 9.4 | 1.0 | 1,800 |

Table 6-continued

| Salt added | Initial pH | Final pH | Growth | Protease activity (U/ml) |
|---|---|---|---|---|
| " 0.2% | 8.7 | 9.5 | 0.9 | 1,580 |
| " 0.3% | 9.1 | 9.6 | 1.0 | 1,300 |
| Na$_2$CO$_3$ 0.2% | 9.5 | 9.6 | 0.9 | 1,020 |
| " 1.0% | 10.3 | 9.8 | 0.8 | 420 |

*adjusted with HCl

Thus, under the foregoing culture conditions, each of the said microorganisms, Bacillus sp. No. 221, Bacillus sp. No. 0-4 and Bacillus sp. No. Y-76, preincubated in the same medium, is inoculated in the medium, and this is shakecultured under appropriate condition, such as 24 - 75 hours at 37° C. After completion of the culture, cells are removed, the broth is neutralized with acetic acid or a similar acid, or not neutralized, and then an organic solvent like ethanol or acetone is added to precipitate the alkaline protease produced. The precipitate is then dehydrated and dried to obtain the objective substance.

The activity of the alkaline protease so obtained is ca. 3,000 U/ml, the said alkaline protease has an optimal pH in the alkaline side of around 11.5. This alkaline protease does not lose its activity even when heated at 50° C for 1 hour, proved by the result of experiments.

Physicochemical properties of the enzyme of this invention, alkaline protease, are as follows:

1. Analytical values: Found: C, 48.04; H, 6.62; N, 16.07; S*, 0.31% * Value calculated from amino acid analysis, which showed that only methionine is present as sulfurcontaining amino acid, and neither cysteine nor cystine are detected.

2. Molecular weight: The following experiments suggest that the molecular weight of this protease is around 20,000 - 30,000.
   i. Sedimentation constant from ultracentrifugation is about 3.3S.
   ii. Molecular weight determined using Sephadex (the word "Sephadex" is a registered trade mark.) was a value between 20,000 and 40,000.
   iii. The value presumed from amino acid analysis is integral multiple of ca. 16,000.
   iv. Molecular weight calculated by the Archibald method is ca. 33,000.

3. Optimal pH and range of stable pH: As will be clear from FIG. 4, the optimal pH lies between 11 and 12. The crystalline enzyme of the present invention, with buffer solution of various pH's, was heated at 60° C for 10 minutes, and the residual activity was determined. Its result is shown in FIG. 5.

| Buffer solutions used: | | pH |
|---|---|---|
| All in 0.05 M | Acetate buffer | 4 - 6 |
| | Phosphate buffer | 6 - 8 |
| | $NaHCO_3$ — $Na_2CO_3$ buffer | 9 - 10.7 |
| | $Na_2HPO_4$ — NaOH buffer | 11 - 12 |

4. Assay of Enzyme Activity:

One milliliter of the enzyme solution suitably diluted with $10^{-2}$M $CaCl_2$ was mixed with 5 ml of 0.6% casein solution (pH 11.5, $2 \times 10^{-2}$M $Na_2HPO_4$- NaOH buffer) at 30° C. After 10 minutes' incubation, 5 ml of trichloroacetic acid solution (0.11M trichloroacetic acid, 0.22M sodium acetate, and 0.33M acetic acid) was added to the reaction mixture and the mixture was further incubated at 30° C for 30 minutes. The mixture was filtered and the absorbance of the filtrate was measured at 275 m$\mu$. The readings were corrected by substracting the value of the blank in which the enxyme solution was mixed with trichloroacetic acid solution before the casein solution was added.

DEFINITION OF ENZYME ACTIVITY:

One unit of protease activity is defined as the amount of enzyme required to produce the digest which is not precipitated by trichloroacetic acid and which gives absorbance value equivalent to 1 $\gamma$ of tyrosine per minute at 30° C. The relative activity is the activity at any pH divided by the maximum activity and multiplied by 100. FIG. 4 of this application gives the data of the absolute activity (arbitrary scale) on the ordinate and the pH's on the axis of the abscissa. The term "arbitrary scale" means that the values of the absolute activity have been reduced to a scale 1/10 the enzyme activity so that the maximum activity instead of being 11.8, is actually a value 10 time as much, that is 118. The relative activity, for instance at pH 7, is the absolute activity at that pH which is about 10 divided by 118 and multiplied by 100. This gives a value of about 8% at pH 7.

5. Range of Working Temperature:

The enzyme activity was measured by the usual method varying the temperature. The measurement was carried out using solutions with and without the addition of 5mM of $CaCl_2$ as a stabilizer. As shown in FIG. 6, when the activity at 30° C is taken as 100%, the activity at 60° - 70° C, in the presence of $CaCl_2$, was 700% and the activity at 60° C, without the addition of $CaCl_2$, was 500%. All the experiments were carried out at pH 11.5.

6. Conditions for Inactivation by Temperature:

The crystalline enzyme of the present invention was dissolved in M/20 Tris buffer of pH 7.0, the solution was heated for 15 minutes at various temperatures, the and residual activity was measured. The measurement was made in the presence or absence of 5mM $CaCl_2$. As shown in FIG. 7, the residual activity was 100% when heated at ca. 30° - 62° C in the presence of $CaCl_2$, and 50% when heated at ca. 65° C. When $CaCl_2$ was not added, residual activity was 100% when heated at about 30° - 52° C and 80% when heated at about 57° C.

7. Inhibition, Activation, and Stabilization:

Inhibition and activation of the crystalline enzyme of the present invention were examined and the result is given in Table 7.

Table 7

| Additive | Concentration (M) | Residual activity (%) |
|---|---|---|
| EDTA (ethylenediaminetetraacetic acid) | $10^{-2}$ | 100 |
| PCMB (p-chloromercuribenzoate) | $10^{-3}$ | 100 |
| Urea | 6 | 0 |

With respect to stabilization against heat, addition of 5mM $CaCl_2$ caused about 10° C stabilization. (Cf. conditions for inactivation by temperature in section (6) and FIG. 7).

8. Method of Purification:

To 1 liter (3,000 U/ml) of the culture filtrate obtained by the culture of the microorganism of the present invention, each of Bacillus sp. No. 221, Bacillus sp. No. 0-4 and Bacillus sp. No. Y-76, 5 liters of acetone were added, the precipitate formed was collected, and washed several times with acetone. About 32 g of acetone-dried powder were obtained. This was washed thoroughly with 100% saturated $(NH_4)_2SO_4$, dissolved in 0.01M phosphate buffer of pH 7.5, and dialyzed overnight against the same buffer.

This dialyzate was passed through a column of Diethylaminoethyl-cellulose (DEAE-cellulose) equilibrated with 0.01M phosphate buffer (pH 7.5). The enzyme of the present invention, alkaline protease, was not adsorbed and passed through the column. The effluent was then passed through a column of carboxymethyl-cellulose (CM-cellulose) equilibrated with the same buffer by which the enzyme was completely adsorbed 100%. The adsorbed alkaline protease was eluted with 0.01M phosphate buffer (pH 7.5) containing 0.3M NaCl.

Thus purified enzyme forms columnar crystals in 30% saturated solution with ammonium sulfate. The yield of the enzyme of the present invention from the above purification procedure is ca. 50%, and the specific activity of the said enzyme is ca. 13,000 U/ml.

9. Crystal Structure:

Fine structure of the enzyme of the present invention is not clear but the crystals formed by the use of ammonium sulfate appear in a resette of columnar crystals as shown in the photomicrograph of FIG. 8.

10. Electrophoresis:

The isoelectric point of the enzyme of the present invention was measured by the Tiselius apparatus and was found to be around pH 10.

Summing up, comparison of the physicochemical properties of the enzyme of the present invention, alkaline protease, with those of the known alkaline proteases indicates clearly that this is a novel alkaline protease which is different from any of the known alkaline proteases.

EFFICACY IN PRACTICAL USE

Figure 1:
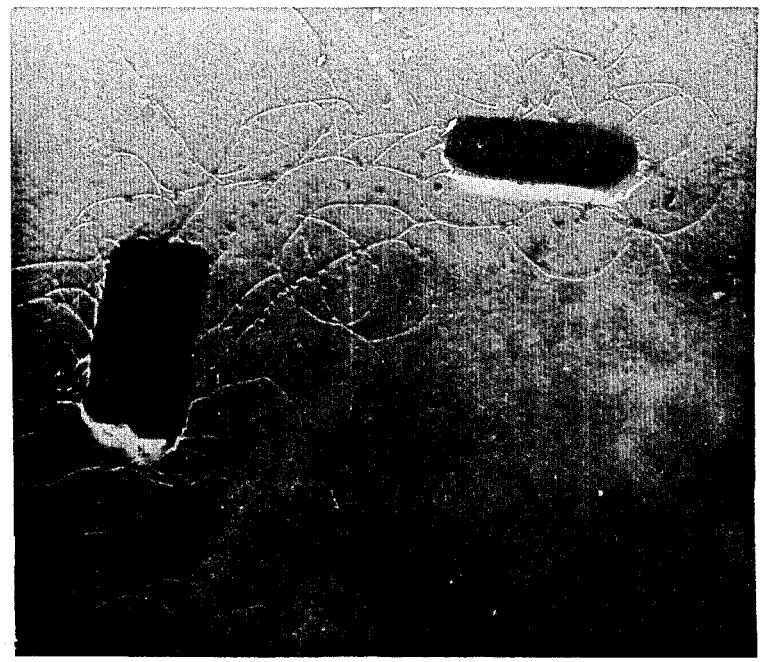
FIG. 1 is an electron photomicrograph of the microorganism used in the present invention, Bacillus sp. No. 221.
Figure 2:
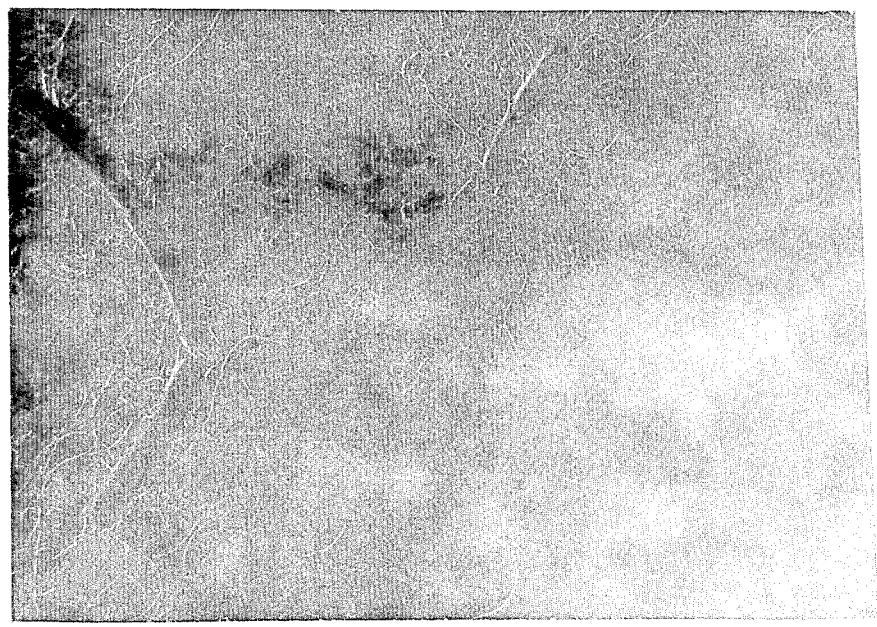
FIG. 2 is an electron photomicrograph of the microorganism used in the present invention, Bacillus sp. No. 0-4.
Figure 3:
FIG. 3 is an electron photomicrograph of the microorganism used in the present invention, Bacillus sp. No. Y-76.
Figure 8:
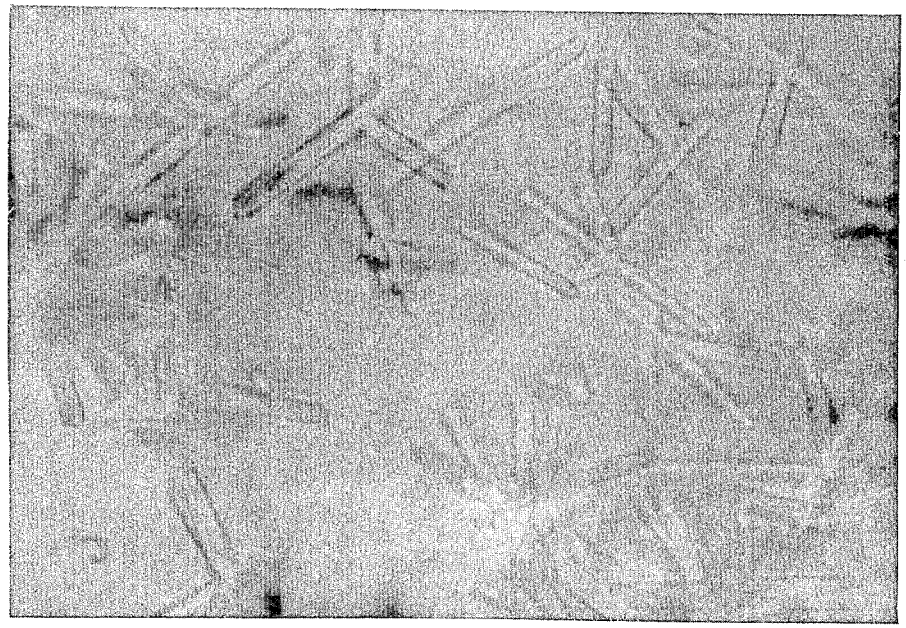
FIG. 8 is a photomicrograph of the crystals of the alkaline protease of this invention.
Figure 4:
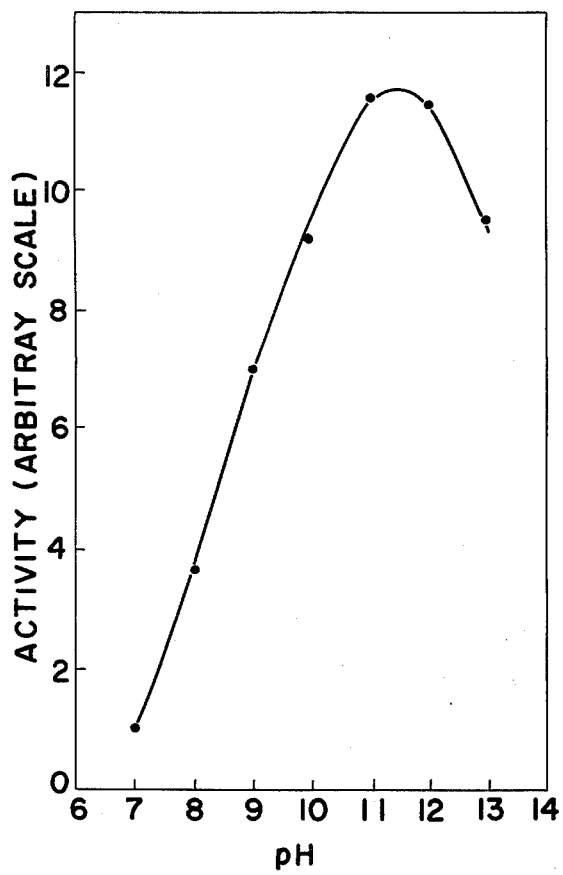
FIG. 4 is a graph showing the optimal pH of the alkaline protease of this invention.
Figure 6:
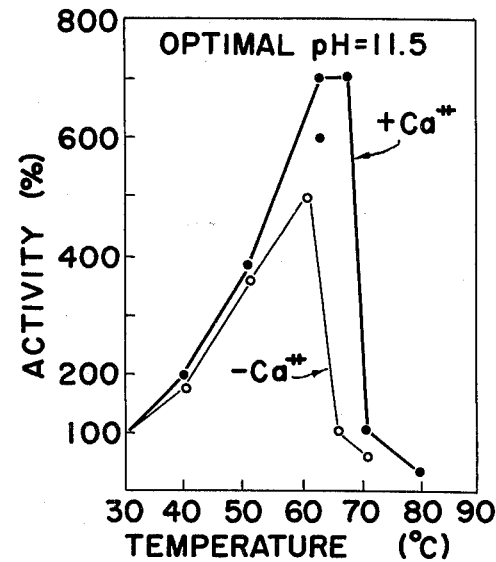
FIG. 6 is a graph showing the range of working temperature of the alkaline protease of this invention.
Figure 7:
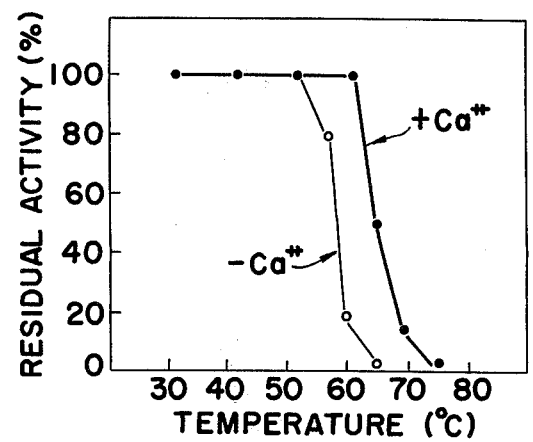
FIG. 7 is a graph showing conditions for inactivation of the alkaline protease of this invention by temperature.
Figure 5:
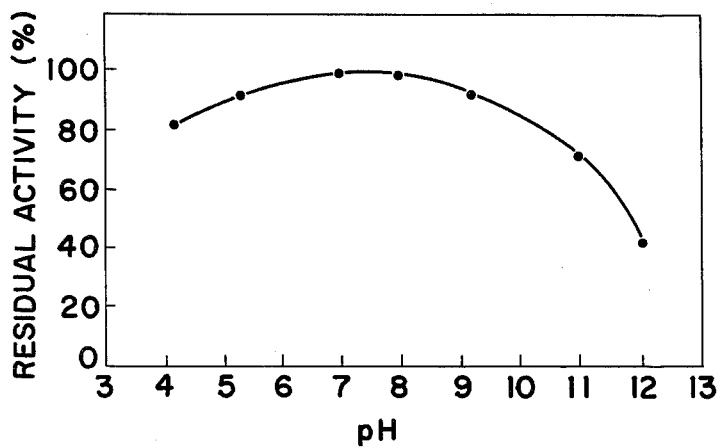
FIG. 5 is a graph showing residual activity of the alkaline protease of this invention by the effect of pH.

The enzyme of this invention, alkaline protease, is a protein-decomposing enzyme that has an optimal pH in the alkaline side (pH around 11.5), shows excellent enzymatic activity when used with detergents, and fortifies the washing power of the detergent.

The enzymatic activity of this alkaline protease in detergents will be explained below as the efficacy of the enzyme of this invention based on experimental rerults.

1. Usage: When the enzyme of this invention is to be used as an additive for detergents, the crystalline enzyme of this invention is directly added to detergents, such as sodium dodecylbenzenesulfonate (DBS) and sodium lauryl sulfate, or mixed with other additives such as polyethyleneglycol. There is no limitation in this preparation, such as the pH of the detergent, or the mixing ratio of detergent components and additives. For example, the use of 0.01 – 1.0% by weight of the enzyme preparation of Example 1 of this invention gives good efficacy, i.e., a good proteolytic power will appear.

2. Efficacy (Enzymatic Activity in Detergents):

The enzyme of this invention was incubated for a definite length of time at various temperatures, in the presence of a detergent, and residual activity of the said enzyme was measured.

Experimental method

The concentration of the detergent at the time of contact with the enzyme of this invention was 0.1%. Sodium dodecylbenzenesulfonate (DBS) and sodium lauryl sulfate were used as the detergents. The pH was adjusted to 10.5 at the time of the reaction by the use of a borate buffer.

| Reaction solution: | |
| --- | --- |
| Detergent, 0.5% | 2 ml |
| Borate buffer (0.05M) | 3 ml |
| Crystalline enzyme of this invention 1 ml (1,000 U/ml) | |
| Additive for water | 4 ml |

Result:
Residual Activity of the Enzyme of this Invention (1)
(Reaction temperature: 50° C)

| Detergents | Additive | Residual activity (%) | | |
| --- | --- | --- | --- | --- |
| | | 0 min | 30 min | 60 min |
| Sodium dodecyl- benzenesulfonate | None | 100 | — | 10 |
| | $CaCl_2$ 5m $\underline{M}$ 0.02% Polyethyleneglycol (Polymerization deg. 2000) | 100 | 95 | 94 |
| Sodium lauryl sulfate | None | 100 | — | 5–15 |
| | $CaCl_2$ 5m $\underline{M}$ 0.02% Polyethylene glycol (Polym. deg. 2000) | 100 | 100 | 100 |

Residual Activity of the Enzyme of this Invention (2)
(Stability against temperature)
(Contact time: 15 min.)

| Detergents | Additive | Residual activity (%) | | | |
| --- | --- | --- | --- | --- | --- |
| | | 50° C | 55° C | 60° C | 65° C |
| Sodium dodecyl- benzenesulfonate | $CaCl_2$ 5m $\underline{M}$ 0.02% Polyethyleneglycol (polymerization deg: 2000) | 100 | 100 | 49 | 10 |

As indicated in the above data, residual activity of the enzyme of this invention is excellent and it was found that stability of the enzyme is markedly increased by the combined use of additives such as $CaCl_2$ and polyethylene-glycol.

SUMMARY OF THE INVENTION

An alkaline protease of the present invention is a novel protease which is produced by the culture of a novel strain of a microorganism selected from the group consisting of Bacillus sp. No. 221 (ATCC 21522), Bacillus sp. No. 0–4 (ATCC 21536) and Bacillus sp. No. Y-76 (ATCC 21537) in a culture medium containing a carbonate, inorganic materials, a nitrogen source, and a carbon source, or a medium containing no sugar, and isolating the alkaline protease produced in the culture medium.

Based on the physicochemical properties of the said alkaline protease, this alkaline protease has been determined as a novel enzyme compared with the known alkaline proteases.

Experiments for the practical use of the said alkaline protease indicate that the said protease is extremely useful as an additive for detergents.

Practical examples in the use of this invention are given below:

EXAMPLE 1

| Medium composition: | |
| --- | --- |
| Glucose | 10 g |
| $K_2HPO_4$ | 1 g |
| Yeast extract | 5 g |
| Peptone | 5 g |
| $MgSO_4 \cdot 7H_2O$ | 0.25 g |

The above composition is dissolved in 900 ml of water and sterilized at 115° C for 15 minutes. A solution of 10 g of anhydrous sodium carbonate dissolved in 100 ml of water is sterilized at 115° C for 15 minutes. These two solutions are mixed to prepare a culture medium of around pH 10.5, 50 ml of which is placed in shouldered shaking flasks (Sakaguchi flasks) of 500-ml capacity. The said Bacillus sp. No. 221 (ATCC 21522), preincubated in the same medium overnight, is inoculated in these flasks, and the flasks are shake-cultured at 37° C for 48 hours. The cells are removed from the culture, and 1 ml of this culture filtrate contained 2,700 units of alkaline protease.

This culture broth was thoroughly cooled and 3 volumes of ethanol were added, by which the enzyme precipitated quantitatively. This precipitate was thoroughly washed with ethanol and dried in air. About 11 g of powder were obtained from one liter of the culture broth.

The sample thereby obtained has an optimal pH around 11.5, and it was found to be an alkaline protease which did not lose its activity even when heated at 50° C for 1 hour (Specific activity, 240,000 U/g).

EXAMPLE 2

| Medium composition: | |
|---|---|
| Wheat bran | 5 g |
| Yeast extract | 0.1 g |
| Corn meal | 0.5 g |

The above composition is placed in an Erlenmeyer flask containing 250 ml of water and sterilized at 115° C for 20 minutes. To this solution, 7 ml of 1% sodium carbonate solution, sterilized at 115° C for 15 minutes, is added, and mixed well. One platinum loop of the said Bacillus sp. No. 221 (ATCC 21522) is inoculated in this medium and the flasks are static cultured at 37° C for 48 hours, with occasional swirling. The protease was extracted with 30 ml of water and its activity was 2,900 U/ml. The sample so obtained was proved to be the alkaline protease having an optimal pH of around 11.5 and which did not lose its activity, even when heated at 50° C for 1 hour.

EXAMPLE 3

| Medium composition: | |
|---|---|
| Yeast extract | 5 g |
| Peptone | 5 g |
| $K_2HPO_4$ | 1 g |
| $MgSO_4 \cdot 7H_2O$ | 0.25 g |

The above composition is dissolved in 1000 ml of water, sterilized at 115° C for 15 minutes to prepare a culture medium of around pH 7.0 – 7.2, and 50 ml of this culture medium is placed in shouldered shaking flasks (Sakaguchi flasks) of 500-ml capacity. The said Bacillus sp. No. 221 (ATCC 21522 ), preincubated in the same medium over-night, is inoculated in these flasks, and shake-cultured at 37° C for 48 hours. The cells were removed and the activity of alkaline protease in this culture filtrate was 1,950 U/ml.

This culture filtrate was thoroughly cooled and 3 volumes of ethanol were added, by which the enzyme precipitated quantitatively. This precipitate was collected, washed thoroughly with ethanol, and air-dried. About 250 mg of dried powder were obtained from 100 ml of the culture broth.

The sample so obtained was proved to be the alkaline protease having an optimal pH of around 11.5 and its activity was not lost, even when heated at 50° C for 1 hour.

EXAMPLE 4

| Medium composition: | |
|---|---|
| $K_2HPO_4$ | 1 g |
| Yeast extract | 5 g |
| Peptone | 5 g |
| $MgSO_4 \cdot 7H_2O$ | 0.25 g |

The above composition is dissolved in 900 ml of water and the solution is sterilized at 115° C for 15 minutes. A 1% solution of $NaHCO_3$ is sterilized at 115° C for 15 minutes and 100 ml of this solution are mixed with the above solution to prepare a culture medium. 50 ml of the culture medium are poured into shouldered shaking flasks (Sakaguchi flasks) of 500-ml capacity. The said Bacillus sp. No. 221 (ATCC 21522 ), preincubated in the same medium over-night, is inoculated in these flasks, and shake-cultured at 37° C for 48 hours. The cells were removed and the alkaline protease in this culture filtrate was 2,500 U/ml.

This culture filtrate was thoroughly cooled, 5 volumes of acetone were added to it, and the enzyme produced precipitated quantitatively. This precipitate was collected, washed with acetone, and air-dried. About 1.2 g of brownish powder were obtained from one liter of the culture broth.

The sample thereby obtained was proved to be the alkaline protease having an optimal pH of around 11.5 and which did not lose its activity, even when heated at 50° C for 1 hour (activity: 1,900,000/g).

EXAMPLE 5

| Medium composition: | |
|---|---|
| Soluble starch | 20 g |
| $K_2HPO_4$ | 1 g |
| Yeast extract | 5 g |
| Peptone | 5 g |
| $MgSO_4 \cdot 7H_2O$ | 0.2 g |

The above composition is dissolved in 900 ml of water and sterilized at 115° C for 15 minutes. A solution of 10 g of anhydrous sodium carbonate dissolved in 100 ml of water is sterilized at 115° C for 15 minutes. These two solutions are mixed to prepare a culture medium of about pH 10.5, 50 ml of which is placed in shouldered shaking flasks (Sakaguchi flasks) of 500 -ml capacity. The said Bacillus sp. No. Y-76 (ATCC 21537), preincubated in the same medium overnight, is inoculated in these flasks, and the flasks are shake-cultured at 37° C for 72 hours. The cells are removed from the culture, and 1 ml of this culture filtrate contained 4,500 unites of alkaline protease.

This culture broth was thoroughly cooled and 3 volumes of ethanol were added, by which the enzyme precipitated quantitatively. This precipitate was thoroughly washed with ethanol and dried in air. About 11 g of powder were obtained from one liter of the culture broth.

The same thereby obtained has an optimal pH around 11.5, and it was found to be an alkaline protease which did not lose its activity even when heated at 50° C. for 1 hour (Specific activity: 400,000 U/g).

EXAMPLE 6

| Medium composition: | |
|---|---|
| Soluble starch | 20 g |
| $K_2HPO_4$ | 1 g |
| Yeast extract | 5 g |
| Peptone | 5 g |
| $MgSO_4 \cdot 7H_2O$ | 0.2 g |

A solution of 10 g of potassium bicarbonate dissolved in 100 ml of water is sterilized at 115° C for 15 minutes. These two solutions are mixed to prepare a culture medium of pH around 10.5, 50 ml of which is placed in shouldered shaking flasks (Sakaguchi flasks) of 500-ml capacity. The said Bacillus sp. No. Y-76 (ATCC 21537), preincubated in the same medium overnight, is inoculated in these flasks, and the flasks are shake-cultured at 37° C for 72 hours.

The cells are removed from the culture, and 1 ml of this culture filtrate contained 3,100 unites of alkaline protease.

This culture broth was thoroughly cooled and 3 volumes of ethanol were added, by which the enzyme precipitated quantitatively. This precipitate was thoroughly washed with ethanol and dried in air. About 11 g of powder were obtained from one liter of the culture broth.

The sample thereby obtained has an optimal pH around 12.0 (Specific activity: 300,000 U/g).

EXAMPLE 7

| Medium composition: | |
|---|---|
| Soluble starch | 20 g |
| $K_2HPO_4$ | 1 g |
| Yeast extract | 5 g |
| Peptone | 5 g |
| $MgSO_4 \cdot 7H_2O$ | 0.2 g |

The above composition is dissolved in 900 ml of water and the solution is sterilized at 115° C for 15 minutes. A 1% solution of $NaHCO_3$ is sterilized at 115° C for 15 minutes and 100 ml of this solution are mixed with the above solution to prepare a culture medium. 50 ml of the culture medium are poured into shouldered shaking flasks (Sakaguchi flasks) of 500 -ml capacity. The said Bacillus sp. No. 0-4 (ATCC 21536), preincubated in the same medium overnight, is inoculated in these flasks, and shake-cultured at 37° C for 72 hours. The cells were removed and the alkaline protease in this culture filtrate was 7,500 U/ml.

This culture filtrate was thoroughly cooled, 5 volume of acetone were added to it, and the enzyme produced precipitated quantitatively. This precipitate was collected, washed with acetone, and air-dried. About 12 g of brownish powder were obtained from one liter of the culture broth.

The sample thereby obtained was proved to be the alkaline protease having an optimal pH of around 12.0 and which did not lose its activity, even when heated at 50° C for 1 hour (Activity: 620,000 U/g).

What we claim is:

1. A process for preparing a novel alkaline protease which is a columnar crystalline powder, having a molecular weight of about 33,000 by the Archibald method, with analytical values of 48.04% carbon, 6.62% hydrogen, 16.07% nitrogen, 0.31% sulfur, the balance being oxygen, having an optimal activity at pH about 11.5, the relative activity being about 8%, 32%, 58%, 80%, 97% and 80% respectively at pH 7, 8, 9, 10, 11 and 13 with casein as the substrate, said enzyme exhibiting an isoelectric point of about 10 and a sedimentation constant of about 3,3S, comprising inoculating Bacillus sp. No. 221 (ATCC 21522) in a culture medium, in which no sugars are contained and having the composition of a carbonate, a carbon source other than a carbonate, a nitrogen source, and an inorganic material, cultering said Bacillus in said culture medium at pH 6 to 10 for a period sufficient to impart substantial proteolytic enzyme activity to said culture medium and to produce said alkaline protease in said medium, and collecting said alkaline protease from said culture medium.

2. A process according to claim 1, wherein said culturing is under aerobic submerged condition with stirring.

3. A process according to claim 1, wherein said culturing is at a temperature of about 24° to 45° C.

4. A process according to claim 1, wherein said culturing is for about 24 to 75 hours.

* * * * *